United States Patent
Callahan et al.

(10) Patent No.: US 11,717,795 B2
(45) Date of Patent: Aug. 8, 2023

(54) CELL BAG ROTATOR

(71) Applicants: Novartis AG, Basel (CH); The Trustees of the University of Pennsylvania, Philadelphia, PA (US)

(72) Inventors: Thomas Callahan, East Hanover, NJ (US); Charles Duffy, Jr., East Hanover, NJ (US)

(73) Assignees: Novartis AG, Basil (CH); The Trustees of the University of Pennsylvania, Philadelphia, PA (US)

( * ) Notice: Subject to any disclaimer, the term of this patent is extended or adjusted under 35 U.S.C. 154(b) by 8 days.

(21) Appl. No.: 17/501,957

(22) Filed: Oct. 14, 2021

(65) Prior Publication Data

US 2022/0241741 A1  Aug. 4, 2022

Related U.S. Application Data

(63) Continuation of application No. 16/038,860, filed on Jul. 18, 2018, now Pat. No. 11,154,827, which is a continuation of application No. PCT/US2017/013868, filed on Jan. 18, 2017.

(60) Provisional application No. 62/280,548, filed on Jan. 19, 2016.

(51) Int. Cl.
| | |
|---|---|
| *B01F 29/322* | (2022.01) |
| *C12M 1/00* | (2006.01) |
| *C12M 3/04* | (2006.01) |
| *B01F 29/62* | (2022.01) |
| *B01F 29/80* | (2022.01) |
| *C12M 1/10* | (2006.01) |
| *B01F 29/00* | (2022.01) |

(52) U.S. Cl.
CPC ........... *B01F 29/322* (2022.01); *B01F 29/62* (2022.01); *B01F 29/80* (2022.01); *C12M 1/10* (2013.01); *C12M 23/14* (2013.01); *C12M 27/10* (2013.01); *B01F 29/4033* (2022.01); *B01F 29/4034* (2022.01)

(58) Field of Classification Search
CPC .. B01F 9/0021; B01F 9/04; B01F 9/10; B01F 2009/0063; B01F 2009/0065; C12M 1/10; C12M 23/14; C12M 27/10; C12N 5/0612; C07K 2319/00
USPC ...................................................... 435/289.5
See application file for complete search history.

(56) References Cited

U.S. PATENT DOCUMENTS

| | | | | |
|---|---|---|---|---|
| 3,625,485 A * | 12/1971 | Adler | ...................... | B01F 31/24 356/246 |
| 5,374,811 A * | 12/1994 | Kiel | ...................... | H05B 6/642 219/710 |
| 6,228,636 B1 * | 5/2001 | Yahiro | ................. | G01N 35/028 435/303.1 |
| 8,109,477 B1 * | 2/2012 | Blasbalg | ................. | B65F 1/004 248/101 |
| 9,212,344 B2 * | 12/2015 | Tsumura | ................. | C12M 29/10 |

\* cited by examiner

*Primary Examiner* — Michael L Hobbs
*Assistant Examiner* — Lenora A Abel
(74) *Attorney, Agent, or Firm* — Frost Brown Todd LLP (57) ABSTRACT

A cell bag rotator is constructed to slowly agitate a plurality of cell bags by rotation along a rotation axis that is at least partially horizontal. The cell bag rotator comprises a plurality of plates to which a respective cell bag is attached. The cell bag rotator is suitable for mixing cells with particles for performing various types of subsequent cell therapy processes on the cells.

16 Claims, 5 Drawing Sheets

CELL BAG ROTATOR

CROSS-REFERENCE TO RELATED APPLICATION

The present application is a continuation of U.S. patent application Ser. No. 16/038,860, filed Jul. 18, 2018, which is a continuation of International Patent Application No. PCT/US2017/013868 filed Jan. 18, 2017, which claims the benefit of U.S. Provisional Patent Application No. 62/280,548 filed Jan. 19, 2016, which are incorporated herein by reference as if reproduced in their entirety.

TECHNICAL FIELD

The present disclosure broadly relates to systems and methods for agitating cell bags containing a eukaryotic cell suspension, particularly a mammalian cell suspension, such as a cell culture. The systems and methods, more specifically relate to a cell bag rotator.

BACKGROUND

Cells may be placed and maintained in a suspension for any of a variety of reasons. For instance, Cells are often grown in cell culture, which is a type of cell suspension, to expand their numbers, particularly of cells selected based on a particular characteristic. In cell culture, cells need access to nutrients, growth-inducers, if present, and sometimes articles to which growth-inducers are bound, such as coated particles. Although these components, if present, are in the cell culture medium, they may become locally depleted around a cell or cells and particles may settle and cells become deprived of these components unless the cell culture is agitated. Prokaryotic cells, such as bacteria, can tolerate simple shaking on a flat shaker. Eukaryotic cells, however, are less robust and will rupture or not grow well if agitated in such a violent manner.

Rotators for test tubes containing eukaryotic cells are available, but these rotators are not suitable for use with eukaryotic cells in other receptacles.

Eukaryotic cells may also be placed in a cell suspension in which the cells remain viable, but grow very slowly or not at all. Such cell suspensions may be used when labeling, characterizing, or sorting the cells.

SUMMARY

As disclosed herein, a cell bag rotator is a mechanical device that is suitable for slowly agitating sterile bags containing a eukaryotic cell suspension, such as mammalian blood cell mixtures, including an apheresis product mixed with particles, without damaging the cells. The cell suspension may be a cell culture.

In one aspect, a cell bag rotator for slowly agitating cell bags by rotation is disclosed. The cell bag rotator may include a rotator including a rotation rod driven by the rotator, a rotator rod connector coupling the rotation rod to a bag holder, and the bag holder. The bag holder may further include a plurality of plates for holding a respective plurality of cell bags in an orientation perpendicular to the rotation rod. In the bag holder, each of the plates may include at least one respective fastener for attaching to a cell bag. The bag holder may further include a plurality of structural rods for holding the plates parallel to each other and for spacing each of the plates apart from one another by a distance. In the bag holder, the distance may correspond to a thickness of the cell bags. In the cell bag rotator, the rotator may be enabled to rotate the bag holder to collectively agitate the cell bags in a uniform manner.

In any of the disclosed variations, the cell bag rotator may include a base for supporting the rotator. In the cell bag rotator, the base may further include a pivot axis to enable the rotator, the rotator rod, and the bag holder to be adjusted to desired a pivot angle from horizontal, and a pivot axis selector to adjust and fix the pivot angle. In any of the disclosed variations of the cell bag rotator, the base may further include a support rod holder to hold the support rod when the pivot angle is 0°.

In any of the disclosed variations of the cell bag rotator, the pivot angle may be between 0° and 90° from horizontal.

In any of the disclosed variations, the cell bag rotator may include a support rod connector attached to the bag holder at an opposite end from the rotator rod connector, and a support rod attached to the support rod connector. In any of the disclosed variations of the cell bag rotator, the support rod holder may further include a support bearing enabling the support rod to rotate freely within the support rod holder.

In any of the disclosed variations of the cell bag rotator, the plurality of plates may include 10 plates for respectively holding 10 cell bags.

In any of the disclosed variations of the cell bag rotator, the bag holder may further include a first endplate attached to the rotator rod connector and to one end of the structural rods, and a second endplate attached to the support rod connector and to another end of the structural rods.

In any of the disclosed variations, the cell bag rotator may include a plurality of spacers placed over the structural rods in between each of the plates, respectively. In the cell bag rotator, a length of each of the spacers may correspond to the distance between the plates.

In any of the disclosed variations of the cell bag rotator, the plates may be rectangular in shape and the plurality of structural rods may consist of four structural rods located at each corner of each of the plates.

In any of the disclosed variations of the cell bag rotator, the fasteners may include alligator clips.

In any of the disclosed variations of the cell bag rotator, the rotator may be enabled to rotate at 4 revolutions per minute (RPM).

In any of the disclosed variations of the cell bag rotator, the rotator may include an electric motor to rotate the rotation rod.

In any of the disclosed variations of the cell bag rotator, the rotator may be enabled to eccentrically rotate the rotation rod.

BRIEF DESCRIPTION OF THE DRAWINGS

A more complete understanding of the present disclosure and advantages thereof may be acquired by referring to the following description taken in conjunction with the accompanying drawings. In the accompanying drawings, parts shown in dotted lines are optional. The drawings may not be to scale and like numerals are used to refer to like features, in which.

DETAILED DESCRIPTION

As described in further detail herein, the present disclosure relates to systems and methods for agitating cell bags containing eukaryotic cell suspensions, such as cell cultures. It particular, it relates to a cell bag rotator. The cell bag rotator may be usable for slow agitation and mixing of eukaryotic cells in cell bags, with or without particles.

The eukaryotic cells may be mammalian cells, in particular blood cells, such as immune cells, intended for various cell therapy purposes. The cells may be from an apheresis product.

The particles may include paramagnetic particles as well as non-paramagnetic particles that may be coated or otherwise processed for cell therapy purposes. For instance, the particles may be coated with growth-inducers, such as growth-inducer that select for a particular cell type or phenotype useful in cell therapy. The particles may further be removable from the cell suspension to allow the use of the cells in cell therapy.

Although the systems and methods described herein may be used to mix any kind of particle with any type of eukaryotic cell, the cell bag rotator disclosed herein may be particularly well-adapted for use in mixing paramagnetic particles with eukaryotic cells to be used in cell therapy during culture of such cells.

The cell bag rotator disclosed herein may provide for mixing about a horizontal axis or about an intermediate axis that is at least partially horizontal. The cell bag rotator disclosed herein may enable cyclic agitation at an angular velocity that provides for slow flipping of the bags to cause pouring and mixing of the cells and fluid in the bags without damaging the cells. In particular, the motion provided by the cell bag rotator disclosed herein is unlike shaking that is tolerated by prokaryotic cells, but damages eukaryotic cells.

The cell bag rotator disclosed herein is suitable for agitating a suspension of living human cells, including human immune system cells, without damage or undesired cell behavior. Because of the sensitivity of mammalian cells to excessive motion and vibration, many types of conventional mixing apparatus and processes are not suitable for agitating living cells or for mixing living cells with particles for cell therapy purposes and may lead to undesired cell behaviors, cell damage, and even cell death. For example, immune system cells may excrete cytokines when damaged that cause the immune system cells to differentiate in undesirable ways. The cell bag rotator disclosed herein may prevent the release of cytokines as a result of the agitation produced.

The cell bag rotator disclosed herein may enable agitation of cell cultures to provide the cells with adequate access to nutrients, growth-inducers, and particles, when present. The cell bag rotator disclosed herein may also enable agitation of other cell suspensions to allow the cells to remain viable or to allow the cells to be labeled. The cell bag rotator disclosed herein may enable slow agitation of a desired plurality of cell bags simultaneously. The cell bag rotator disclosed herein may be implemented in a modular manner to enable loading and unloading of cell bags in a timely manner. The cell bag rotator disclosed herein may be constructed of materials suitable for use in clean rooms and at various biocompatible ambient conditions.

Figure 1A:
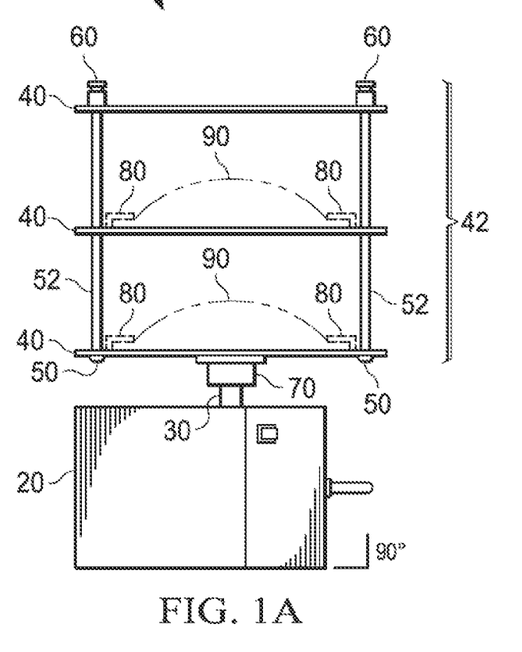
FIG. 1A is a schematic diagram of a cell bag rotator in vertical position.

Referring now to the drawings, FIG. 1A is a schematic diagram of a cell bag rotator 10 in vertical position. As shown, cell bag rotator 10 includes a rotator 20, which may include an internal motor, such as an electric motor (not visible) that rotates a rotation rod 30. Rotator 20 may be enabled to mechanically rotate rotation rod 30 in a circular motion. The circular motion of rotation rod 30 may be centric about a rotation axis, or may be eccentric such that rotation rod undergoes a combination of translation and rotation (see FIG. 2). Rotation rod 30 may be attached to a bag holder 42 using rotator rod connector 70. Bag holder 42 may hold cell bags 90 in place when cell bag rotator 10 is operating. Cell bag rotator 10 may be enabled to provide agitation to a bag holder 42 at an angular velocity corresponding to about 4 rotations per minute (RPM), or between about 3 RPM and 5 RPM, less than about 10 RPM, or less than 15 RPM. In particular implementations, parts of cell bag rotator 10, such as various structural components included therein, may be constructed using stainless steel.

Specifically, bag holder 42 may be implemented using a plurality of plates 40 that are attached to one another using structural rods 50, while rotator rod connector 70 may be attached to a first plate 40 of bag holder 42. Although in FIG. 1A bag holder 42 is shown in an implementation for holding two cell bags 90 (or simply, bags 90) for descriptive clarity, it will be understood that bag holder 42 may be implemented with different numbers of plates 40 to hold different numbers of bags, such as 4, 6, 8, 10, 12, 15, 18, 20 bags, as nonlimiting examples of a plurality of bags that may be simultaneously loaded onto bag holder 42. The plurality of plates 40 may be secured together and spaced using structural rods 50, which may pass through holes in plates 40 (see FIG. 3), along with spacers 52, which provide a standoff distance between each respective plate 40. Accordingly, a number of structural rods 50 may correspond to a given design for plates 40, which may vary in different implementations. When plates 40 are rectangular or substantially rectangular in shape, four structural rods 50 may be used at respective corners of the rectangular shape of plates 40. When plates 40 are another shape, such as circular, different numbers of structural rods 50 may be used. In different implementations, a shape of plate 40 may correspond to a shape of cell bag 90, which may also vary and may include other shapes, such as circular, triangular, square, or other regular or irregular shapes and forms.

Structural rods 50 may be secured at an end of bag holder 42 by structural rod locks 60, which may hold bag holder 42 together. In certain instances, rod locks 60 may be magnetic locks for rapid removal and installation. Rod locks 60 may also be mechanical attachments, such as threaded nuts or pins that penetrate structural rods 50. In certain implementations, spacers 52 may each contact, or be individually secured to, two adjacent plates 40. In certain implementations, pacers 52 may be hollow cylinders that fit over structural rods 50 and may be collectively secured by rod lock 60. It is noted that various different attachment mechanisms, such as threading or friction coupling, may be used to attach structural rods 50 and spacers 52 to plates 40 to assemble bag holder 42. In some implementations, plates 40 may be fixed within bag holder 42, such that bags 90 are inserted through a side opening between structural rods 50 and are attached to plates 40 via the opening.

In certain implementations, such as when bag holder 42 is dimensioned to hold a larger number of bags 90, bag holder 42 may be pre-assembled such that a subset (such as 4, 5, 6, or 8, as nonlimiting examples) of the plurality of plates 40 are loaded with bags 90 and secured to form a bag module (not shown). A plurality of the bag modules may each be respectively populated with bags 90 simultaneously in a parallel work process. Then, the bag modules may be assembled in the vertical position shown in FIG. 1A. In this manner, the bag modules may be loaded with bags 90 in parallel, thereby reducing an overall time for loading a larger number of bags 90 into cell bag rotator 10, instead of loading each bag individually in succession, which may take longer and may exceed a desired time that bags 90 are not being slowly agitated by rotation.

In cell bag rotator 10, each plate 40 includes at least one fastener 80 for attaching bag 90 to plate 40. Fastener 80 may represent any type of fastener for securing bag 90 in a desired position relative to plate 40 and for ensuring that bag 90 does not move or deform in an undesirable manner during agitation. For example, fasteners 80 may be spring-loaded for quick operation to secure and release bags 90. In particular implementations, fastener 80 may be a clip, such as an alligator clip, that clamps externally to at least one surface of bag 90.

In FIG. 1A, cell bag rotator 10 is shown in a vertical position that is suitable for loading and unloading bags, as described above. For many types of cells to which cell therapy processes are applied, rotation about a vertical axis (90° to horizontal), as shown in FIG. 1A, may be undesirable due to the settling effects of gravity that are not counteracted by the rotation, among other factors. In some implementations, cell bag rotator 10 may have a mechanism to prevent rotation of rotator 20 when cell bag rotator 10 is or near the vertical position.

Figure 1B:
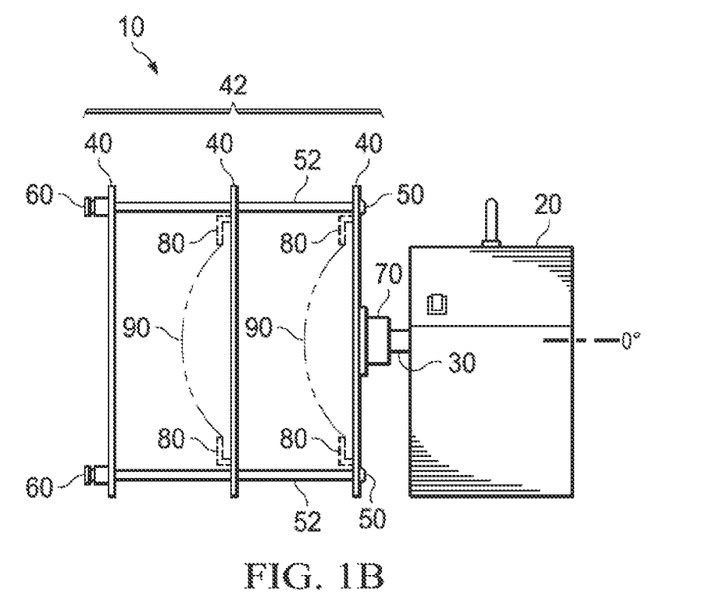
FIG. 1B is a schematic diagram of a cell bag rotator in horizontal position suitable for rotating cells bags.

Referring now to FIG. 1B, cell bag rotator 10 is shown in a horizontal position that may be suitable for agitation and mixing of cells for cell therapy processes. In FIG. 1B, cell bag rotator 10 rotates bag holder 42 about a horizontal axis (0° to horizontal) to which rotation rod 30 is aligned. In this manner, bags 90 are rotated to continuously counteract gravity and enable proper or desired mixing and slow agitation of the contents of bags 90.

Figure 1C:
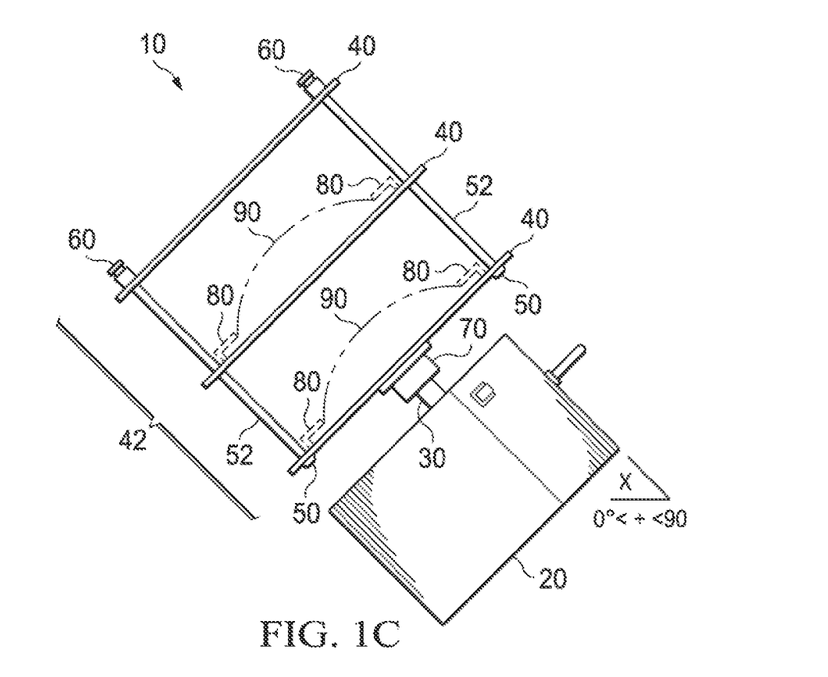
FIG. 1C is a schematic diagram of a cell bag rotator in an intermediate position suitable for rotating cell bags.

Referring now to FIG. 1C, cell bag rotator 10 is shown in an intermediate position that may be suitable for agitation and mixing of cells for cell therapy processes. In FIG. 1C, cell bag rotator 10 rotates bag holder 42 about an intermediate axis (between 0° and 90° to horizontal) to which rotation rod 30 is aligned. In this manner, bags 90 are rotated in a manner that continuously counteracts gravity and enables proper or desired mixing and slow agitation of the contents of bags 90.

Figure 2:
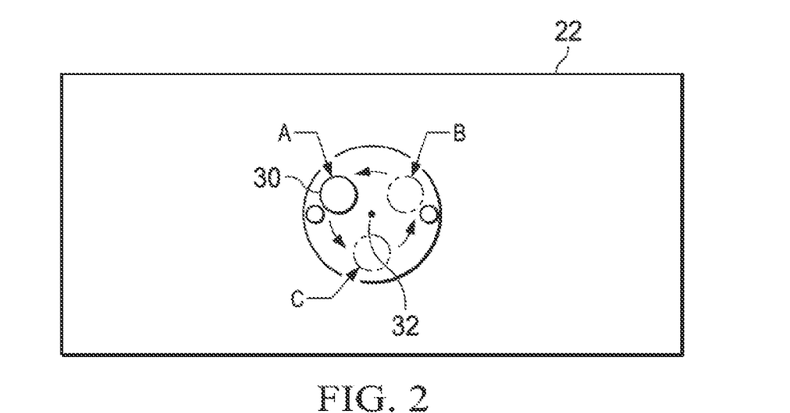
FIG. 2 is a schematic diagram of an end view of a rotator having eccentricity about a rotation axis.

Referring now to FIG. 2, a schematic diagram of an end view of a rotator 22 having eccentricity about a rotation axis 32 is shown. Rotator 22 may represent a particular example of rotator 20 shown in FIGS. 1A, 1B, and 1C with eccentricity. In FIG. 2, rotator 20 causes rotation rod 30 to rotate eccentrically about axis 32. Due to the eccentric arrangement, rotation rod 30 rotates in the counterclockwise direction, as shown, and also translates from position A to position C to position B. In this manner, bag holder 42 (not shown in FIG. 2) may be imparted a certain degree of translation as well as rotation, which may be desirable. It is noted that different degrees of eccentricity may be implemented with rotator 22, for example, by varying a spacing between axis 32 and rotation rod 30. It will be understood that in implementations with eccentricity, rotator 22 is used in conjunction with cell bag rotator 10 that provides sufficient clearance corresponding to the actual eccentricity to enable continuous rotation.

Figure 3:
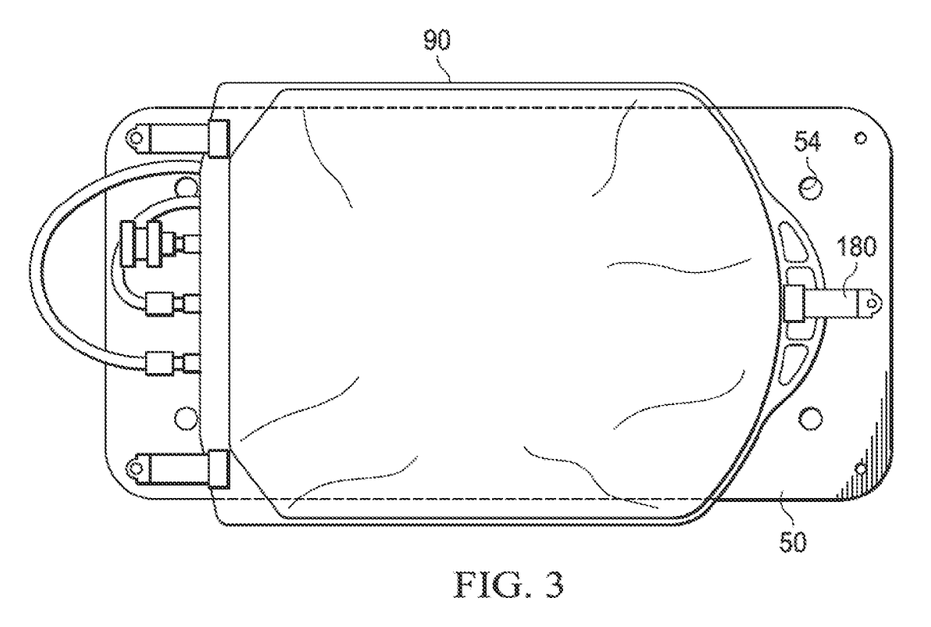
FIG. 3 is a schematic diagram of a top view of a plate with a cell bag secured thereto.

Referring now to FIG. 3, a schematic diagram of a top view of a plate 50 with a cell bag 90 secured thereto is illustrated. Cell bag 90 may be any bag suitable for an apheresis product or any other blood or blood product bag. Cell bag 90 may be formed using two plastic sheets of material that are sealed along an outer edge. Cell bag 90 may be sterile and may include inlet ports and outlet ports to allow cells and fluids to enter and leave. As shown in FIG. 3, cell bag 90 is attached to plate 50 using fasteners 180. In one example, fasteners 180 are spring-loaded clips which may clamp onto one or both surfaces of cell bag 90 to secure cell bag 90 to plate 50. Also visible in FIG. 3 are holes 54 that may be penetrated by structural rods 50, as described previously.

As noted previously, cell bag 90 is suitable for mixing cells with particles, such as paramagnetic particles, in a suspension fluid. The suspension fluid may contain both particle-bound cells and unbound cells. The cells in cell bag 90 may be obtained directly from a biological sample, such as blood, or from a cell culture. The suspension fluid may be any fluid able to support viability of the cells through the process. For instance, the suspension fluid may be a culture medium, a freezing agent, such as a dimethyl sulfoxide (DMSO)-containing fluid, another fluid with a set or controlled pH, or another fluid with nutrients. The suspension fluid may also be a buffer. The suspension fluid may have a different viscosity than the buffer. The cell suspension fluid or buffer may contain antimicrobial agents.

In particular, the suspension fluid may include a culture medium and the cells may be cultured while being rotated by cell bag rotator 10.

The particles in cell bag 90 may be paramagnetic particles that are formed from any paramagnetic or magnetizable material, such as a metal or metal alloy. Typically the paramagnetic material is not toxic to the cells or to any patient who will later receive the cells. The paramagnetic material may be coated to avoid toxicity. The paramagnetic material may be selected to achieve a high magnetic saturation flux ($m_s$).

The paramagnetic particles may be coated with a binding agent, such as a growth agent, a receptor or ligand, an antigen, an antibody, or any binding fragments or chimeric variants thereof, such as a chimeric antigen receptor ligand. The binding agents may be reversible in some instances, allowing detachment of the particles spontaneously or using a particular chemical agent. The binding agents may also include a photo-cleavable linker. In some instances, the coating may interact with the cells. In other instances, the coating may interact with at least one unwanted constituent of the cell suspension that is to be removed. The unwanted constituent may be active or inactive and may have previously served a useful function with respect to the cells or the cell suspension fluid. Example unwanted constituents include antibodies, growth factors, other proteins, and polymers.

Different types of paramagnetic particles, such as particles with different binding agents or formed from different magnetic materials may be present in some cell suspensions, allowing for complex separations or iterative removal of binding agents. Additional, non-paramagnetic particles, which may also be coated with any binding agent, may also be bound to cells.

Other particles that are not paramagnetic may also be present in the cell suspension in cell bags 90 and may be coated with anything used to coat the paramagnetic particles.

Cell bags 90 may be formed from or lined with any biologically compatible material and may be sterile prior to contact with the cell suspension.

Figure 4A:
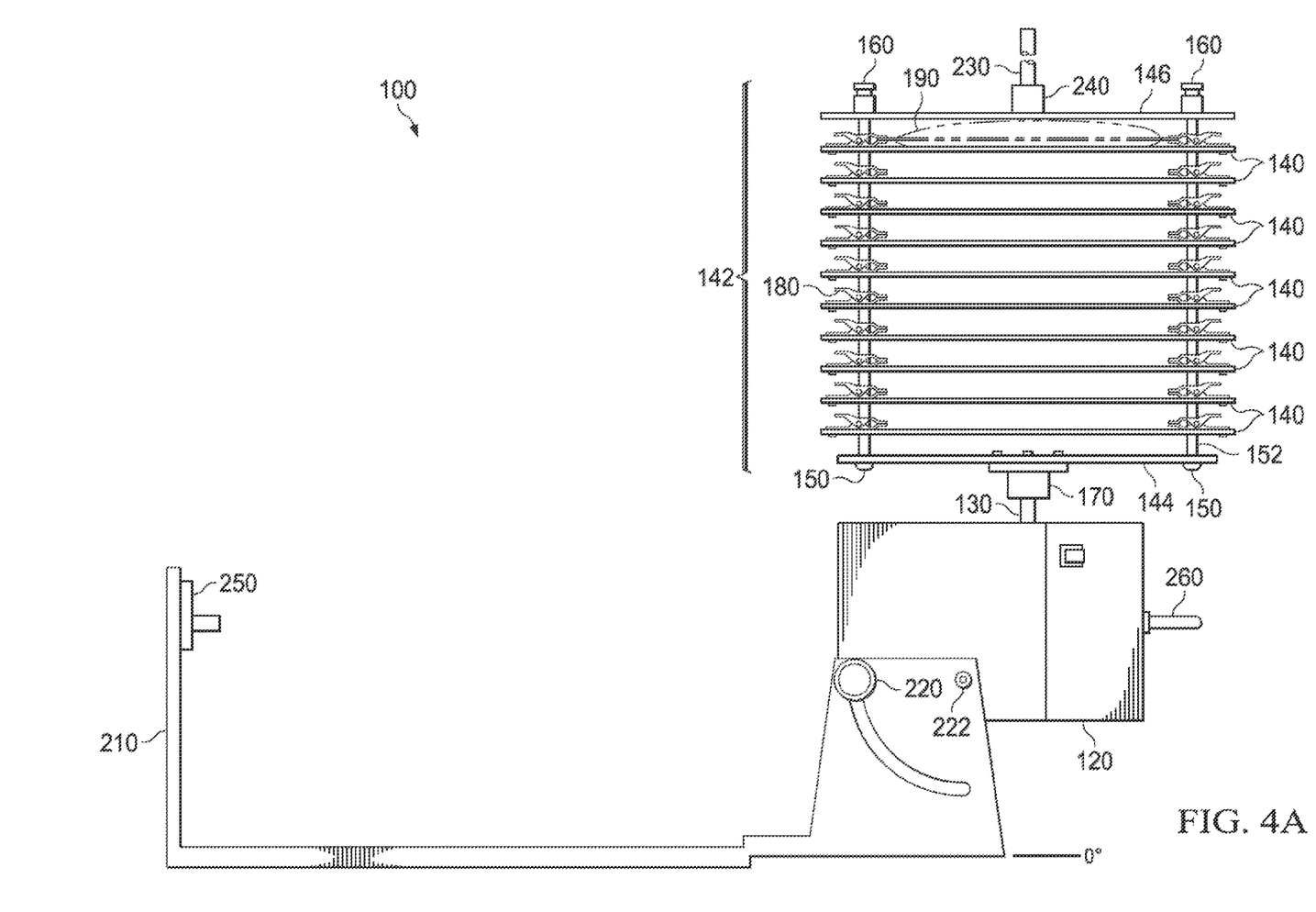
FIG. 4A is a schematic diagram of a 10-bag cell bag rotator in vertical position.

Referring now to FIG. 4A, a schematic diagram of a 10-bag cell bag rotator 100 in vertical position is depicted. Cell bag rotator 100 may be substantially similar to cell bag rotator 10 shown in FIGS. 1A, 1B, and 1C. Although cell bag rotator 100 is shown in an implementation for up to ten bags 190 in FIG. 4A, it will be understood that cell bag rotator 100 may be implemented to support different numbers of bags 190, such as 4, 6, 8, 12, 14, 16, 18, 20, 24, 25, or 30 bags (not shown), as nonlimiting examples. Although FIG. 4A shows bag holder 142 populated with a single bag 190 for descriptive clarity, it will be understood that bag holder 142 can hold up to ten bags 190 corresponding to ten plates 140 (see FIG. 4B). As shown, cell bag rotator 100 includes a rotator 120, which may include an internal motor, such as an electric motor (not visible) that rotates a rotation rod 130. Rotator 120 may be controlled using a power switch to activate or deactivate rotation. In some implementations, rotator 120 may be externally controlled to switch on/off or to control a rotation speed, a rotation direction, an angular velocity, etc. Rotator 120 may be enabled to mechanically rotate rotation rod 130 in a circular motion. The circular motion of rotation rod 130 may be centric about a rotation axis, or may be eccentric such that rotation rod undergoes a combination of translation and rotation (see FIG. 2). Rotation rod 130 may be attached to a bag holder 142 using rotator rod connector 170. Bag holder 142 may hold cell bags 190 in place when cell bag rotator 100 is operating. Also shown with cell bag rotator 100 is base 210 that supports rotator 120. Cell bag rotator 100 may be enabled to provide agitation to bag holder 142 at an angular velocity corresponding to about 4 RPM, or between about 3 RPM and 5 RPM, less than about 10 RPM, or less than 15 RPM.

In FIG. 4A, bag holder 142 is constructed using plates 140, each of which supports, secures, and provides attachment for one bag 190. The plurality of plates 140 may be secured together and spaced by structural rods 150 and spacers 152 and fastened using rod locks 160, in a substantially similar manner as described above with respect to plates 40, structural rods 50, spacers 52, and rod locks in bag holder 42 of FIGS. 1A, 1B, and 1C. Additionally, bag holder 142 comprises a first end plate 144 and a second end plate 146, which may provide additional structural support and rigidity to plates 140. Specifically, rotator rod connector 170 may attach to first end plate 144 at a first end of bag holder 142. At an opposing end of bag holder 142, second end plate 146 may attach to a support rod connector 240 that holds support rod 230. Support rod connector 240 and support rod 230 may be fixed to second end plate 146.

In certain implementations, bag holder 142 may be pre-assembled such that a subset (such as 4, 6, 8, 10 as nonlimiting examples) of plates 140 are loaded with bags 190 and secured to form a bag module (not shown). Then, the bag modules may be assembled in the vertical position shown in FIG. 4A. In this manner, the bag modules may be loaded with bags 190 in parallel, thereby reducing an overall time for loading all of bags 190 into cell bag rotator 100, instead of loading each bag individually in succession, which may take longer and may exceed a desired time that bags 190 are not being slowly agitated by rotation.

In cell bag rotator 100, each plate 140 includes at least one fastener 180 for attaching bag 190 to plate 140. Fastener 180 may represent any type of fastener for securing bag 190 in a desired position relative to plate 40. As shown in the example of FIG. 4A, fastener 180 is an alligator clip that clamps externally to both surfaces of bag 190.

In FIG. 4A, cell bag rotator 100 is shown in a vertical position that is suitable for loading and unloading bags 190, as described above. For many types of cells to which cell therapy processes are applied, rotation about a vertical axis (90° to horizontal, no horizontal axis component), as shown in FIG. 4A, may be undesirable due to the settling effects of gravity that are not counteracted by the rotation, among other factors. The vertical position of cell bag rotator 100 may be enabled by rotation about a pivot axis 222, to which rotator 120 is rotatably attached to base 210. Base 210 may also include pivot axis selector 220, which, for example, may be a knob in a groove. A handle 260 may be used to rotate rotator about pivot axis 222 to select a pivot angle corresponding to the vertical position (pivot angle is 90°), the horizontal position (pivot angle is 0°), or the intermediate position (pivot angle is between 0° and 90°), as described above. In the horizontal position (see FIG. 4B), support rod 230 may rest in a support rod holder 250 at an opposite end of base 210 from rotator 120. In certain instances, support rod holder 250 may include a support bearing (not visible) to facilitate low friction or frictionless free rotation of support rod 230 when the pivot angle is 0°. When rotation rod 130 is enabled for eccentric rotation (see FIG. 2), support rod holder 250 may be similarly constructed to enable support rod 230 (along with bag holder 142) to rotate eccentrically about axis 32.

Figure 4B:
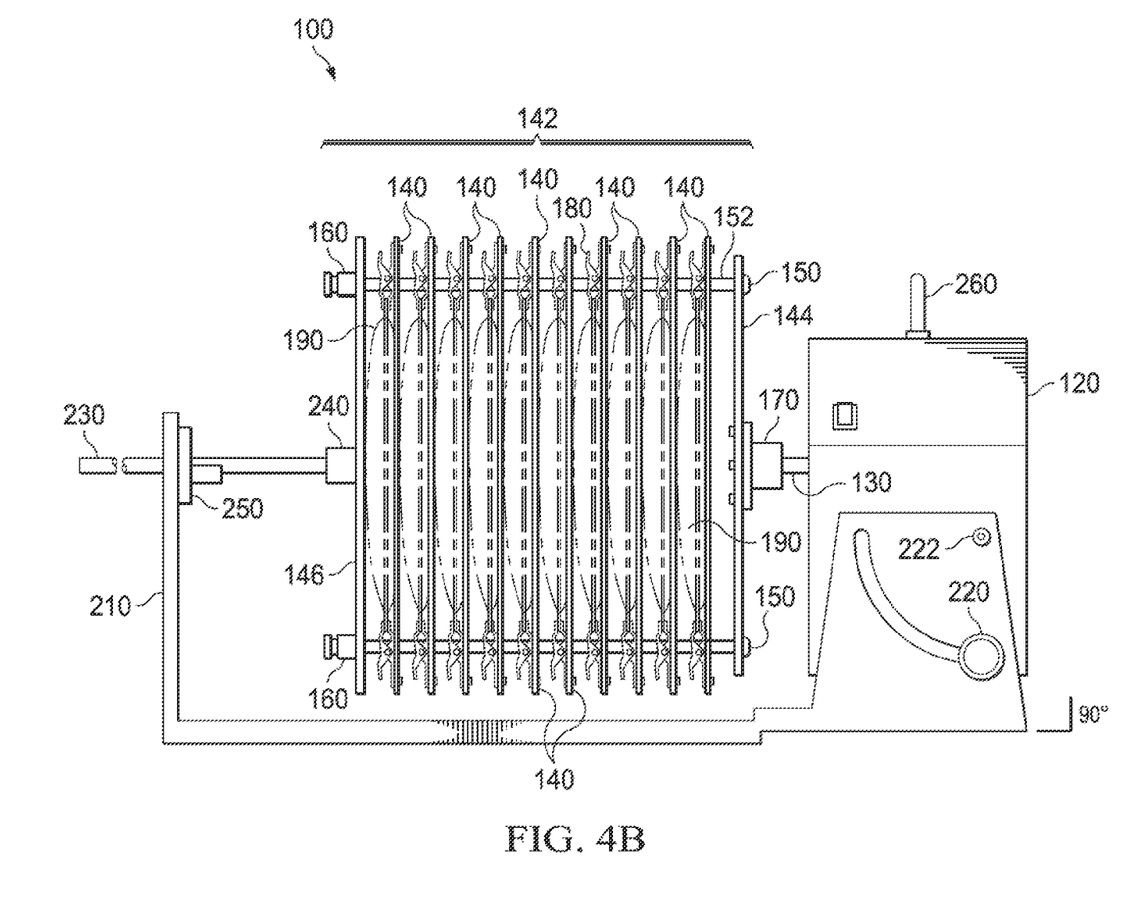
FIG. 4B is a schematic diagram of a 10-bag cell bag rotator in horizontal position.

Referring now to FIG. 4B, a schematic diagram of cell bag rotator 100 in horizontal position populated with ten bags 190 is depicted. Specifically, in FIG. 4B, pivot axis selector 220 corresponds to the horizontal position (pivot angle is 0°) and may include a detention mechanism to maintain the horizontal position. Also in FIG. 4B, support rod 230 rests in support rod holder 250, which enables support rod 230 (and bag holder 142) to rotate in the horizontal position. Support rod holder 250 may include a bearing to enable free rotation of support rod 230 with little or no friction.

Clinical Applications

The cell bag rotator described herein may be suitable for use with processes that are conducted according to clinical good manufacturing practice (cGMP) standards. The processes may be used for cell purification, enrichment, harvesting, washing, concentration or for cell media exchange, particularly during the collection of raw, starting materials (i.e. cells) at the start of a manufacturing process, as well as during the manufacturing process for the selection or expansion of cells for cell therapy.

Particles may be present in the external environment of cells for any number of reasons. For example, particles may be coated with a growth-inducer, which causes responsive cells in a mixed-cell or single-cell culture to grow and divide. Particles may also be coated with a binding agent, which attaches to a particular type of cell, allowing it to be separated from other types of cells in the same mixed-cell suspension. This separation based on cell type allows desirable cells to be separated from undesirable cells.

In order to attach particles to cells for various cell therapy purposes, the particles are typically mixed with a cell source population, such as blood, an apheresis product, or other blood products.

The cells may include any plurality of cells. The cells may be of the same cell type, or mixed cell types. In addition, the cells may be from one donor, such as an autologous donor or a single allogenic donor for cell therapy. The cells may be obtained from patients by, for example, leukapheresis or apheresis. The cells may include T cells, for example may include a population that has greater than 50% T cells, greater than 60% T cells, greater than 70% T cells, greater than 80% T cells, or 90% T cells.

In one such process, described here by way of example, cells, for example, T cells, are collected from a donor (for example, a patient to be treated with an autologous chimeric antigen receptor T cell product) via apheresis (e.g., leukapheresis). Collected cells may then be optionally purified, for example, by an elutriation step. Paramagnetic particles, for example, anti-CD3/anti-CD28-coated paramagnetic particles, may then be added to the cell population, to expand the T cells. The process may also include a transduction step, wherein nucleic acid encoding one or more desired proteins, for example, a CAR, for example a CAR targeting CD19, is introduced into the cell. The nucleic acid may be introduced in a lentiviral vector. The cells, e.g., the lentivirally transduced cells, may then be expanded for a period of days, for example, 1, 2, 3, 4, 5, 6, 7, 8, 9, 10, or more days, for example in the presence of a suitable medium.

The systems and methods disclosed herein for operating a cell bag rotator may similarly benefit other cell therapy products by wasting fewer desirable cells, causing less cell trauma, and more reliably mixing magnetic and non-paramagnetic particles with cells, as compared to conventional systems and methods.

As disclosed herein, a cell bag rotator is constructed to slowly agitate a plurality of cell bags by rotation along a rotation axis that is at least partially horizontal. The cell bag rotator comprises a plurality of plates to which a respective cell bag is attached. The cell bag rotator is suitable for mixing cells with particles for performing various types of subsequent cell therapy processes on the cells.

Although only exemplary embodiments of the disclosure are specifically described above, it will be appreciated that modifications and variations of these examples are possible without departing from the spirit and intended scope of the disclosure. In addition, the systems and methods may include additional components and steps not specifically described herein. Furthermore, embodiments may include only a portion of the systems described herein for use with the methods described herein.

What is claimed is:

1. A cell bag rotator, comprising:
   a rotation rod comprising a first end and a second end opposite the first end;
   a bag holder coupled to the first end of the rotation rod, the bag holder, comprising:
      a plurality of plates for holding a respective plurality of cell bags in an orientation perpendicular to the rotation rod, wherein each of the plates includes at least one respective fastener for attaching to a cell bag;
   a rotator coupled to the second end of the rotation rod and configured to rotate the rotation rod about a first axis of rotation to agitate any cell bags attached to the bag holder;
   a base supporting the rotator and comprising a pivot axis enabling rotation of the bag holder about a second axis of rotation orthogonal to the first axis of rotation.

2. The cell bag rotator of claim 1, wherein the base further comprising a pivot axis selector configured to allow for selection of an amount of rotation of the bag holder about the second axis of rotation from between 0 degrees and 90 degrees from horizontal.

3. The cell bag rotator of claim 2, wherein the pivot axis selector comprises a knob engaged within a groove defined by the base.

4. The cell bag rotator of claim 2, further comprising a support rod coupled to a first end of the bag holder, wherein the first end of the rotation rod is coupled to a second end of the bag holder opposite the first end of the bag holder.

5. The cell bag rotator of claim 4, further comprising a support rod holder to support the support rod when the bag holder is positioned at an angle of 0 degrees from horizontal.

6. The cell bag rotator of claim 5, wherein the support rod holder comprises a support rod bearing enabling the support rod to rotate freely within the support rod holder.

7. The cell bag rotator of claim 1, wherein the plurality of plates includes 10 plates for respectively holding 10 cell bags.

8. The cell bag rotator of claim 1, further comprising a rotator rod connector attached to an exterior surface of the bag holder and coupling the first end of the rotation rod to the bag holder.

9. The cell bag rotator of claim 1, wherein the bag holder further comprises:
   a plurality of structural rods for holding the plates parallel to each other and for spacing each of the plates apart from one another by a distance, the distance corresponding to a thickness of the cell bags.

10. The cell bag rotator of claim 9, further comprising:
    a support rod coupled to a first end of the bag holder, wherein the first end of the rotation rod is coupled to a second end of the bag holder opposite the first end of the bag holder, wherein the bag holder further comprises:
       a first endplate of the plurality of plates coupled to the first end of the rotation rod and to a first end of the plurality of structural rods; and
       a second endplate of the plurality of plates coupled to the support rod and to a second end of the plurality of structural rods opposite the first end of the plurality of structural rods.

11. The cell bag rotator of claim 10, further comprising:
    a plurality of spacers placed over the structural rods in between each of the plates, respectively, wherein a length of each of the spacers corresponds to the distance between the plates.

12. The cell bag rotator of claim 9, wherein the plates are rectangular in shape and the plurality of structural rods consists of four structural rods located at each corner of each of the plates.

13. The cell bag rotator of claim 1, wherein the fasteners comprise alligator clips.

14. The cell bag rotator of claim 1, wherein the rotator is enabled to rotate at 4 revolutions per minute.

15. The cell bag rotator of claim 1, wherein the rotator comprises an electric motor to rotate the rotation rod.

16. The cell bag rotator of claim 1, wherein the first axis of rotation is offset from a center of the bag holder such that the bag holder is subject to eccentric rotation in response to rotation of the rotation rod.

* * * * *

UNITED STATES PATENT AND TRADEMARK OFFICE
CERTIFICATE OF CORRECTION

PATENT NO. : 11,717,795 B2
APPLICATION NO. : 17/501957
DATED : August 8, 2023
INVENTOR(S) : Thomas Callahan and Charles Duffy, Jr.

It is certified that error appears in the above-identified patent and that said Letters Patent is hereby corrected as shown below:

On the Title Page

Column 1 - reads "(73) Assignees: Novartis AG, Basil (CH)"; which should be deleted and replaced with "(73) Assignees: Novartis AG, Basel (CH)"

Signed and Sealed this
Second Day of January, 2024

Katherine Kelly Vidal
*Director of the United States Patent and Trademark Office*